(12) United States Patent
Braig et al.

(10) Patent No.: US 8,372,765 B2
(45) Date of Patent: Feb. 12, 2013

(54) ODOR INHIBITING WATER-ABSORBING COMPOSITES

(75) Inventors: Volker Braig, Weinheim-Lützelsachsen (DE); Thomas Daniel, Waldsee (DE)

(73) Assignee: BASF SE, Ludwigshafen (DE)

( * ) Notice: Subject to any disclaimer, the term of this patent is extended or adjusted under 35 U.S.C. 154(b) by 3 days.

(21) Appl. No.: 13/011,507

(22) Filed: Jan. 21, 2011

(65) Prior Publication Data

US 2011/0182845 A1  Jul. 28, 2011

Related U.S. Application Data

(60) Provisional application No. 61/298,578, filed on Jan. 27, 2010.

(51) Int. Cl.
*B32B 5/16* (2006.01)

(52) U.S. Cl. ... 442/118; 442/117; 442/153; 252/186.25; 252/186.27

(58) Field of Classification Search .............. 252/186.25, 252/186.27; 442/117, 118, 153
See application file for complete search history.

(56) References Cited

U.S. PATENT DOCUMENTS

| 1,953,526 | A   | * | 4/1934 | Ainslie et al. | 604/359 |
| 6,852,904 | B2  | * | 2/2005 | Sun et al.     | 604/359 |
| 2003/0098115 | A1 | * | 5/2003 | Dodge et al. | 156/167 |
| 2011/0053767 | A1 | * | 3/2011 | Braig et al. | 502/402 |

FOREIGN PATENT DOCUMENTS

| GB | 627512   | A | 8/1949 |
| GB | 2377890  | A | 1/2003 |
| JP | 2001039802 | A | 2/2001 |
| JP | 2001115042 | A | 4/2001 |

OTHER PUBLICATIONS

Buchholz, Fredric L., et al.. *Modern Superabsorbent Polymer Technology*, "Commercial Processes for the Manufacture of Superabsorbent Polymers," pp. 252-258, pp. 71-103. New York: John Wiley & Sons, Inc., 1998.

* cited by examiner

*Primary Examiner* — Ali Soroush

(74) *Attorney, Agent, or Firm* — Marshall, Gerstein & Borun LLP

(57) ABSTRACT

The present invention relates to a process for producing odor-inhibiting water-absorbing composites comprising water-absorbing polymer particles and fibers, wherein the fibers are premixed with at least one metal peroxide, metal hyperoxide or metal ozonide.

14 Claims, No Drawings

ODOR INHIBITING WATER-ABSORBING COMPOSITES

CROSS-REFERENCE TO RELATED APPLICATIONS

This application claims the benefit of U.S. provisional application No. 61/298,578, filed Jan. 27, 2010, incorporated herein by reference in its entirety.

The present invention relates to a process For producing odor-inhibiting water-absorbing composites comprising water-absorbing polymer particles and fibers, wherein the fibers are premixed with at least one metal peroxide, metal hyperoxide or metal ozonide.

The production of hygiene articles is described in the monograph "Modern Superabsorbent Polymer Technology", F. L. Buchholz and A. T. Graham, Wiley-VCH 1998, pages 252 to 258.

Hygiene articles consist typically of an upper liquid-pervious topsheet, a lower liquid-impervious layer and a water-absorbing composite between the topsheet and the layer. The composite consists of water-absorbing polymers and fibers. Further layers are, for example, absorption and distribution layers and/or tissue layers.

The production of water-absorbing polymer particles is likewise described in the monograph "Modern Superabsorbent Polymer Technology", F. L. Buchholz and A. T. Graham, Wiley-VCH, 1998, pages 71 to 103. The water-absorbing polymer particles are also referred to as superabsorbents.

The properties of the water-absorbing polymer particles can be adjusted via the degree of crosslinking. With rising degree of crosslinking, the gel strength increases and the absorption capacity falls. This means that the centrifuge retention capacity (CRC) decreases with rising absorbency under load (AUL) (at very high degrees of crosslinking, the absorbency under load also decreases again).

To improve the performance properties, for example saline flow conductivity (SFC) in the swollen gel bed in the diaper, and absorbency under load (ALL), water-absorbing polymer particles are generally postcrosslinked. This increases only the degree of crosslinking of the particle surface, which can at least partly decouple absorbency under load (ALL) and centrifuge retention capacity (CRC). This postcrosslinking can be carried out in aqueous gel phase. Preference is given, however, to surface coating ground and screened-off polymer particles (base polymer) with a postcrosslinker, thermally postcrosslinking and drying. Crosslinkers suitable for this purpose are compounds which comprise at least two groups which can form covalent bonds with the carboxylate groups of the hydrophilic polymer.

GB 627,512 discloses the use of zinc peroxide for odor inhibition in hygiene articles.

GB 2 377 890 describes oxidizing agents as odor-inhibiting additives in water-absorbing compositions.

JP 2001/39802 teaches the use of sodium percarbonate and sodium perborate as antimicrobial additives for water-absorbing compositions.

JP 2001/115042 discloses water-absorbing compositions comprising water-absorbing polymer particles, inorganic peroxides and ethylenediaminetetraacetic acid.

It was an object of the present invention to provide improved odor-inhibiting water-absorbing composites.

The object was achieved by a process for producing odor-inhibiting water-absorbing composites, comprising water-absorbing polymer particles and fibers, which comprises premixing the fibers with at least one metal peroxide, metal hyperoxide or metal ozonide.

The metal peroxide is preferably the peroxide of a metal of main group 1, of main group 2 and/or of transition group 2 of the Periodic Table of the Elements, more preferably the peroxide of a metal of transition group 2 of the Periodic Table of the Elements, most preferably zinc peroxide.

Suitable metal peroxides are, for example, lithium peroxide, strontium peroxide, barium peroxide, sodium peroxide, magnesium peroxide, calcium peroxide, potassium hyperoxide and zinc peroxide. The metal peroxides are typically present in the form of mixtures with their oxides, for example zinc peroxide with zinc oxide.

To prevent corrosion, the metal peroxides, metal hyperoxides or metal ozonides should comprise a minimum level of halide such as chloride, preferably less than 500 ppm, more preferably less than 200 ppm, most preferably less than 10 ppm.

The composite comprises preferably 0.001 to 5% by weight, preferably from 0.01 to 3% by weight, more preferably from 0.1 to 1.5% by weight, most preferably from 0.2 to 0.8% by weight, of the metal peroxide, metal hyperoxide or metal ozonide.

The composite comprises preferably from 10 to 90% by weight, more preferably from 30 to 80% by weight, most preferably from 50 to 70% by weight, of fibers. The preferred fibers are cellulose fibers.

The present invention is based on the finding that the odor-inhibiting action of metal peroxides, metal hyperoxides and metal ozonides, especially zinc peroxide, can be enhanced significantly by premixing with the fibers.

The inventive composites comprise preferably less than 50 ppm, more preferably less than 10 ppm, most preferably less than 5 ppm, of heavy metal ions. Heavy metal ions, especially iron ions, lead to catalytic destruction of the metal peroxides, metal hyperoxides and metal ozonides, and hence lower the storage stability of the composites.

The production of the water-absorbing polymer particles and of the composites will be explained in detail hereinafter.

The water-absorbing polymer particles are produced, for example, by polymerizing a monomer solution or suspension comprising a) at least one ethylenically unsaturated monomer which bears acid groups and may be at least partly neutralized,
b) at least one crosslinker,
c) at least one initiator,
d) optionally one or more ethylenically unsaturated monomers copolymerizable with the monomers mentioned under a) and
e) optionally one or more water-soluble polymers, and are typically water-insoluble.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer is, for example, acrylic acid purified according to WO 2004/035514 A1 comprising 99.8460% by weight of acrylic acid, 0.0950% by weight of acetic acid, 0.0332% by weight or water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, preferably at least 10 ppm by weight, more preferably at least 30 ppm by weight, especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers h) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A 1, EP 0 559 476 A1, EP 0 632 068 A1, WO 93/21237 A1 WO 2003/104299 A1 WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 404/\), WO 90/15830 A1 and WO 2002/032962 A2.

Preferred crosslinkcrs b) are pentaerythrityl triallyl ether, tetraalloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and or propoxylated glycerol, especially the triacrylate of 3-tuply ethoxylated glycerol.

The amount of crosslinker h) is preferably 0.05 to 1.5% by weight, more preferably 0.1 to 1% by weight, most preferably 0.3 to 0.6% by weight, based in each case on monomer a). With rising crosslinker content, the centrifuge retention capacity (CRC) falls and the absorbency under a load of 21.0 g/cm$^2$ (AUL0.3 psi) passes through a maximum.

The initiators c) used may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as BRÜGGOLITE® FF6 and BRÜGGOLITE® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight, most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel, which has to be comminuted in a further process step, for example in an extruder or kneader.

However, it is also possible to dropletize an aqueous monomer solution and to polymerize the droplets obtained in a heated carrier gas stream. This allows the process steps of polymerization and drying to be combined, as described in WO 2008/040715 A2 and WO 2008/052971 A1.

The acid groups of the resulting polymer gels have typically been partially neutralized. Neutralization is preferably carried out at the monomer stage. This is typically done by mixing in the neutralizing agent as an aqueous solution or preferably also as a solid. The degree of neutralization is preferably from 25 to 85 mol %, for "acidic" polymer gels more preferably from 30 to 60 mol %, most preferably from 35 to 55 mol %, and for "neutral" polymer gels more preferably from 65 to 80 mol %, most preferably from 70 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts, such as the salt of triethanolamine. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably 10 to 30 mol % and more preferably 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The polymer gel is then preferably dried with a belt drier until the residual moisture content is preferably 0.5 to 15% by weight, more preferably 1 to 10% by weight, most preferably 2 to 8% by weight, the residual moisture content being determined by EDANA recommended test method No. WSP 230.2-05 "Moisture Content". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size (fines) are obtained. The solids content of the gel before the drying is preferably from 25 to 90% by weight, more preferably from 35 to 70% by weight, most preferably from 40 to 60% by weight. Optionally, it is, however, also possible to use a fluidized bed drier or a paddle drier for the drying operation.

Thereafter, the dried polymer gel is ground and classified, and the apparatus used for grinding may typically be single- or multistage roll mills, preferably two- or three-stage roll mills, pin mills, hammer mills or vibratory mills.

The mean particle size of the polymer particles removed as the product fraction is preferably at least 200 µm, more preferably from 250 to 600 µm, very particularly from 300 to 500 µm. The mean particle size of the product fraction may be determined by means of EDANA recommended test method No. WSP 220.2-05 "Particle Size Distribution", where the proportions by mass of the screen fractions are plotted in cumulative form and the mean particle size is determined graphically. The mean particle size here is the value of the mesh size which gives rise to a cumulative 50% by weight.

The proportion of particles with a particle size of at least 150 µm is preferably at least 90% by weight, more preferably at least 95% by weight, most preferably at least 98% by weight.

Polymer particles with too small a particle size lower the saline flow conductivity (SFC). The proportion of excessively small polymer particles (fines) should therefore be small.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible in later process steps to remove excessively small polymer particles, for example after the surface postcrosslinking or another coating step. In this case, the excessively small polymer particles recycled are surface postcrosslinked or coated in another way, for example with fumed silica.

When a kneading reactor is used for polymerization, the excessively small polymer particles are preferably added during the last third of the polymerization.

When the excessively small polymer particles are added at a very early stage, for example actually to the monomer solution, this lowers the centrifuge retention capacity (CRC) of the resulting water-absorbing polymer particles. However, this can be compensated, for example, by adjusting the amount of crosslinker b) used.

When the excessively small polymer particles are added at a very late stage, for example not until an apparatus connected downstream of the polymerization reactor, for example to an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 µm is preferably at least 90% by weight, more preferably at least 95% by weight, most preferably at least 98% by weight.

The proportion of particles having a particle size of at most 600 µm is preferably at least 90% by weight, more preferably at least 95% by weight, most preferably at least 98% by weight.

Polymer particles with too great a particle size lower the swell rate. The proportion of excessively large polymer particles should therefore likewise be small.

Excessively large polymer particles are therefore typically removed and recycled into the grinding of the dried polymer gel.

To further improve the properties, the polymer particles can be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amidoamines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidone and its derivatives, such as 2-hydroxyethyl-2-oxazolidone in DE 198 07 502 A1, bis- and poly-2-oxazolidinones in DE 198 07

992 C1,2-oxotetrahydro-1,3-oxazine and its derivatives in DE 198 54 573 A1, N-acyl-2-oxazolidones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and its derivatives in WO 2003/031482 A1.

Preferred surface postcrosslinkers are ethylene carbonate, ethylene glycol diglycidyl ether, reaction products of polyamides with epichlorohydrin, and mixtures of propylene glycol and 1,4-butanediol.

Very particularly preferred surface postcrosslinkers are 2-hydroxyethyloxazolidin-2-one, oxazolidin-2-one and 1,3-propanediol.

In addition, it is also possible to use surface postcrosslinkers which comprise additional polymerizable ethylenically unsaturated groups, as described in DE 37 13 601 A1.

The amount of surface postcrosslinkers is preferably 0.001 to 2% by weight, more preferably 0.02 to 1% by weight, most preferably 0.05 to 0.2% by weight, based in each case on the polymer particles.

In a preferred embodiment, polyvalent cations are applied to the particle surface in addition to the surface postcrosslinkers before, during or after the surface postcrosslinking.

The polyvalent cations usable are, for example, divalent cations such as the cations of zinc, magnesium, calcium and strontium, trivalent cations such as the cations of aluminum, tetravalent cations such as the cations of titanium and zirconium. Possible counterions are, for example, chloride, bromide, sulfate, hydrogensulfate, carbonate, hydrogencarbonate, nitrate, phosphate, hydrogenphosphate, dihydrogenphosphate and carboxylate, such as acetate and lactate. Aluminum sulfate and aluminum lactate are preferred. Apart from metal salts, it is also possible to use polyamines as polyvalent cations.

The amount of polyvalent cation used is, for example, 0.001 to 1.5% by weight, preferably 0.005 to 1% by weight, more preferably 0.02 to 0.8% by weight, based in each case on the polymer particles.

The surface postcrosslinking is typically performed in such a way that a solution of the surface postcrosslinker is sprayed onto the dried polymer particles. After the spraying, the polymer particles coated with surface postcrosslinker are dried thermally, and the surface postcrosslinking reaction can take place either before or during the drying.

The spraying of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal PFLUGSCHARG® plowshare mixers (Gebr. Lödige Maschinenbau GmbH; Paderborn; Germany), Vrieco-Nauta continuous mixers (Hosokawa Micron By; Doetinchem; the Netherlands), Processall Mixmill mixers (Processall Incorporated; Cincinnati; US) and Schugi FLEXOMIX® (Hosokawa Micron BV; Doetinchem; the Netherlands). However, it is also possible to spray on the surface postcrosslinker solution in a fluidized bed.

The surface postcrosslinkers are typically used in the form of an aqueous solution. The content of nonaqueous solvent and/or total amount of solvent can be used to adjust the penetration depth of the surface postcrosslinker into the polymer particles.

When exclusively water is used as the solvent, a surfactant is advantageously added. This improves the wetting performance and reduces the tendency to form lumps. However, preference is given to using solvent mixtures, for example isopropanol/water, 1,3-propanediol/water and propylene glycol/water, where the mixing ratio by mass is preferably from 20:80 to 40:60.

The thermal drying is preferably carried out in contact driers, more preferably paddle driers, most preferably disk driers. Suitable driers are, for example, Hosokawa BEPEX® horizontal paddle driers (Hosokawa Micron GmbH; Leingarten; Germany), Hosokawa BEPEX® disk driers (Hosokawa Micron GmbH; Leingarten; Germany) and NARA paddle driers (NARA Machinery Europe; Frechen; Germany). Moreover, it is also possible to use fluidized bed driers.

The drying can be effected in the mixer itself, by heating the jacket or blowing in warm air. Equally suitable is a downstream drier, for example a shelf drier, a rotary tube oven or a heatable screw. It is particularly advantageous to mix and dry in a fluidized bed drier.

Preferred drying temperatures are in the range of 100 to 250° C., preferably 120 to 220° C., more preferably 130 to 210° C., most preferably 150 to 200° C. The preferred residence time at this temperature in the reaction mixer or drier is preferably at least 10 minutes, more preferably at least 20 minutes, most preferably at least 30 minutes, and typically at most 60 minutes.

Subsequently, the surface postcrosslinked polymer particles can be classified again, excessively small and/or excessively large polymer particles being removed and recycled into the process.

To further improve the properties, the surface postcrosslinked polymer particles can be coated or remoisturized.

The remoisturizing is carried out preferably at 30 to 80° C., more preferably at 35 to 70° C. and most preferably at 40 to 60° C. At excessively low temperatures, the water-absorbing polymer particles tend to form lumps, and, at higher temperatures, water already evaporates noticeably. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging.

Suitable coatings for improving the swell rate and the saline flow conductivity (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

The water-absorbing polymer particles have a moisture content of preferably 1 to 15% by weight, more preferably 2 to 10% by weight, most preferably 3 to 5% by weight, the moisture content being determined by EDANA recommended test method No. WSP 230.2-05 "Moisture Content".

The water-absorbing polymer particles have a centrifuge retention capacity (CRC) of typically at least 15 g/g, preferably at least 20 g/g, preferentially at least 22 g/g, more preferably at least 24 g/g, most preferably at least 26 g/g. The centrifuge retention capacity (CRC) of the water-absorbing polymer particles is typically less than 60 g/g. The centrifuge retention capacity (CRC) is determined by EDANA recommended test method No. WSP 241.2-05 "Centrifuge Retention Capacity".

The water-absorbing polymer particles have an absorbency under a load of 49.2 g/cm² of typically at least 15 g/g, preferably at least 20 g/g, preferentially at least 22 g/g, more preferably at least 24 g/g, most preferably at least 26 g/g. The absorbency under a load of 49.2 g/cm² of the water-absorbing polymer particles is typically less than 35 g/g. The absorbency under a load of 49.2 g/cm² is determined analogously to EDANA recommended test method No. WSP 242.2-05 "Absorption under Pressure", except that a pressure of 49.2 g/cm² is established instead of a pressure 21.0 g/cm².

In addition to the water-absorbing polymer particles, the water-absorbing composite comprises at least one, preferably hydrophilic, fiber material. "Hydrophilic" is understood to mean that aqueous liquids spread rapidly over the fibers. Usually, the fiber material is cellulose, modified cellulose, rayon, polyester such as polyethylene terephthalate. Particular preference is given to cellulose fibers such as chemical pulp. The fibers generally have a diameter of from 1 to 200 µm, preferably from 10 to 100 µm. In addition, the fibers have a minimum length of 1 mm.

A detailed overview of examples of fibers which can be used in the present invention is given by the patent application WO 95/26209 A1, page 28 line 9 to page 36 line 8. Said passage is thus part of this invention.

Examples of cellulose fibers include cellulose fibers which are customarily used in absorption products, such as fluff pulp and cellulose of the cotton type. The materials (soft- or hardwoods), production processes such as chemical pulp, semichemical pulp, chemothermomechanical pulp (CTMP) and bleaching processes are not particularly restricted. For example, natural cellulose fibers such as cotton, flax, silk, wool, jute, ethylcellulose and cellulose acetate are used.

Suitable synthetic fibers are produced from polyvinyl chloride, polyvinyl fluoride, polytetrafluoroethylene, polyvinylidene chloride, polyacrylic compounds such as ORLON®, polyvinyl acetate, polyethyl vinyl acetate, soluble or insoluble polyvinyl alcohol. Examples of synthetic fibers include thermoplastic polyolefin fibers, such as polyethylene fibers (PULPEX®), polypropylene fibers and polyethylene-polypropylene bicomponent fibers, polyester fibers, such as polyethylene terephthalate fibers (DACRON® or KODEL®), copolyesters, polyvinyl acetate, polyethyl vinyl acetate, polyvinyl chloride, polyvinylidene chloride, polyacrylics, polyamides, copolyamides, polystyrene and copolymers of the aforementioned polymers and also bicomponent fibers composed of polyethylene terephthalate-polyethylene-isophthalate copolymer, polyethyl vinyl acetate/polypropylene, polyethylene/polyester, polypropylene/polyester, copolyester/polyester, polyimide fibers (nylon), polyurethane fibers, polystyrene fibers and polyacrylonitrile fibers. Preference is given to polyolefin fibers, polyester fibers and their bicomponent fibers. Preference is further given to thermally adhesive bicomponent fibers composed of polyolefin of the core-sheath type and side-by-side type on account of their excellent dimensional stability following fluid absorption.

The fiber cross section may be round or angular, or else have another shape, for example like that of a butterfly.

The synthetic fibers mentioned are preferably used in combination with thermoplastic fibers. In the course of the heat treatment, the latter migrate to some extent into the matrix of the fiber material present and so constitute bond sites and renewed stiffening elements on cooling. In addition, the addition of thermoplastic fibers means that there is an increase in the present pore dimensions after the heat treatment has taken place. This makes it possible, by continuous metered addition of thermoplastic fibers during the formation of the absorbent layer, to continuously increase the fraction of thermoplastic fibers in the direction of the topsheet, which results in a similarly continuous increase in the pore sizes. Thermoplastic fibers can be formed from a multitude of thermoplastic polymers which have a melting point of less than 190° C., preferably in the range from 75° C. to 175° C. These temperatures are too low for damage to the cellulose fibers to be likely.

Lengths and diameters of the above-described synthetic fibers are not particularly restricted, and generally any fiber from 1 to 200 mm in length and from 0.1 to 100 denier (gram per 9000 meters) in diameter may preferably be used. Preferred thermoplastic fibers are from 3 to 50 mm in length, particularly preferred thermoplastic fibers are from 6 to 12 mm in length. The preferred diameter for the thermoplastic fibers is in the range from 1.4 to 10 decitex, and the range from 1.7 to 3.3 decitex (gram per 10 000 meters) is particularly preferred. The form of the fibers may vary; examples include woven types, narrow cylindrical types, cut/split yarn types, staple fiber types and continuous filament fiber types.

Suitable hydrophilic fibers include for example cellulose fibers, modified cellulose fibers, rayon, polyester fibers, for example polyethylene terephthalate (DACRON®), and hydrophilic nylon (HYDROFIL®). Suitable hydrophilic fibers may also be obtained by hydrophilizing hydrophobic fibers, for example the treatment of thermoplastic fibers obtained from polyolefins (e.g. polyethylene or polypropylene, polyamides, polystyrenes, polyurethanes, etc.) with surfactants or silica. However, for reasons of cost and availability, cellulose fibers are preferred.

In the process according to the invention, the fibers are premixed with the at least one metal peroxide, metal hyperoxide or metal ozonide. The method of mixing is not subject to any restriction. It is possible, for example, to prepare powder mixtures from fibers and metal peroxide, metal hyperoxide or metal ozonide. However, it is also possible to spray on the metal peroxide, metal hyperoxide or metal ozonide as solution or suspension.

In the course of preparation of powder mixtures from fibers and at least one metal peroxide, metal hyperoxide or metal ozonide, it is advantageous to use dedusting agents. Suitable dedusting agents are polyglycerols, polyethylene glycols, polypropylene glycols, random or block copolymers of ethylene oxide and propylene oxide. Further dedusting agents suitable for this purpose are the polyethoxylates or polypropoxylates of polyhydroxyl compounds, such as glycerol, sorbitol, trimethylolpropane, trimethylolethane and pentaerythritol. Examples thereof are n-tuply ethoxylated trimethylolpropane or glycerol, where n is an integer from 1 to 100. Further examples are block copolymers, such as n-tuply (in total) ethoxylated and then m-tuply propoxylated trimethylolpropane or glycerol, where n is an integer from 1 to 40 and m is an integer from 1 to 40. The sequence of the blocks may also be reversed. The dedusting agents may also be diluted with water.

The water-absorbing polymer particles are embedded into the fiber material described. This can be accomplished in various ways, for example by using the water-absorbing polymer particles and the fibers together to form an absorbent layer in the form of a matrix, or by incorporating water-absorbing polymer particles into fiber blend layers, where they are ultimately fixed, whether by means of adhesive or lamination of the layers.

The fluid-acquiring and -distributing fiber matrix may comprise synthetic fiber or cellulose fiber or a mixture of synthetic fiber and cellulose fiber, in which case the blend ratio may vary from (100 to 0) synthetic fiber:(0 to 100)

cellulose fiber. The cellulose fibers used may additionally have been chemically stiffened to increase dimensional stability.

The chemical stiffening of cellulose fibers may be provided in different ways. One way of achieving fiber stiffening is by adding suitable coatings to the fiber material. Such additives include, for example, polyamide-epichlorohydrin coatings (KYMENE® 557 H, Hercules, Inc., US), polyacrylamide coatings (described in U.S. Pat. No. 3,556,932 or as the PAREZ® 631 NC commercial product from American Cyanamid Co., US), melamine-formaldehyde coatings and polyethyleneimine coatings.

Cellulose fibers can also be chemically stiffened by chemical reaction. For example, suitable crosslinkers can be added to bring about crosslinking which takes place within the fiber. Suitable crosslinkers are typical substances which are used to crosslink monomers. They include, but are not limited to, $C_2$-$C_8$-dialdehydes, $C_2$-$C_8$-monoaldehydes having acid functionality and in particular $C_2$-$C_9$-polycarboxylic acids. Specific substances from this group are, for example, glutaraldehyde, glyoxal, glyoxylic acid, formaldehyde and citric acid. These substances react with at least two hydroxyl groups within any one cellulose chain or between two adjacent cellulose chains within any one cellulose fiber. The crosslinking stiffens the fibers, to which greater dimensional stability is imparted as a result of this treatment. In addition to their hydrophilic character, these fibers exhibit uniform combinations of stiffening and elasticity. This physical property makes it possible to retain the capillary structure even under simultaneous contact with fluid and compressive forces and to prevent premature collapse.

Chemically crosslinked cellulose fibers are known and described in WO 91/11162 A1, U.S. Pat. Nos. 3,224,926, 3,440,135, 3,932,209, 4,035,147, 4,822,453, 4,888,093, 4,898,642 and 5,137,537. The chemical crosslinking brings about stiffening of the fiber material, which is ultimately reflected in improved dimensional stability for the composite as a whole. The individual layers are joined together by methods known to the person skilled in the art, for example melting by heat treatment, addition of hot-melt adhesives, latex binders, etc.

Examples of processes to obtain a water-absorbing composite consisting, for example, of a carrier material to which water-absorbing polymer particles are fixed on one or both sides are known and included by the invention but not limited thereto.

Examples of processes to obtain a water-absorbing composite consisting, for example, of water-absorbing polymer particles (c) embedded into a fiber material blend of synthetic fibers (a) and cellulose fibers (b), the blend ratio varying from (100 to 0) synthetic fiber: (0 to 100) cellulose fiber, include (1) a process where (a), (b) and (c) are mixed together at one and the same time, (2) a process where a mixture of (a) and (I)) is mixed into (c), (3) a process where a mixture of (b) and (c) is mixed with (a), (4) a process where a mixture of (a) and (c) is mixed into (b), (5) a process where (b) and (c) are mixed and (a) is continuously metered in, (6) a process where (a) and (c) are mixed and (b) is continuously metered in, and (7) a process where (b) and (c) are mixed separately into (a). Of these examples, processes (1) and (5) are preferred. The apparatus used in this process is not particularly restricted and any customary apparatus known to the person skilled in the art can be used.

The water-absorbing composite obtained in this way can optionally be subjected to a heat treatment, so as to result in an absorption layer having excellent dimensional stability in the moist state. The heat treatment process is not particularly restricted. Examples include heat treatment by feeding hot air or infrared irradiation. The temperature of the heat treatment is in the range from 60° C. to 230° C., preferably from 100° C. to 200° C., particularly preferably from 100° C. to 180° C.

The duration of the heat treatment depends on the type of synthetic fiber, its amount and the hygiene article production rate. Generally the duration of the heat treatment is in the range from 0.5 second to 3 minutes, preferably from 1 second to 1 minute.

The correspondingly produced water-absorbing composite can optionally be subjected to a pressing operation, preferably with a roll press. The rolls may be heated. The gap width defines the degree of pressing. The gap width is typically 1 to 100% of the original thickness of the material.

The water-absorbing composite is generally provided with a liquid-pervious topsheet and a liquid-impervious backsheet. Furthermore, leg cuffs and adhesive tabs are attached to finalize the hygiene article. The materials and types of pervious topsheet and impervious backsheet and of the leg cuffs and adhesive tabs are known to the person skilled in the art and are not particularly restricted. Examples thereof can be found in WO 95/26209 A1.

The present invention further relates to the use of the abovementioned water-absorbing composites in hygiene articles. For example, the hygiene article may have the following construction:
(A) an upper liquid-pervious topsheet
(B) a lower liquid-impervious layer
(C) the water-absorbing composite between topsheet (A) and layer (B),
(D) optionally a tissue layer immediately above and below the water-absorbing, composite
(C) and
(E) optionally an absorption and distribution layer between topsheet (A) and water-absorbing composite (C).

The thickness of the water-absorbing composite can be varied. For example, the water-absorbing composite may have less material, for example, in the outer region. Cutouts and channels are likewise possible.

Hygiene articles are understood to mean, for example, incontinence pads and incontinence pants for adults, or diapers for babies.

The liquid-impervious topsheet (A) is a layer in direct contact with the skin. The material for this purpose consists of customary synthetic or semisynthetic fibers or films of polyester, polyolefins, rayon or natural fibers such as cotton. In the case of nonwoven materials, the fibers should generally be bound by binders such as polyacrylates. Preferred materials are polyester, rayon and blends thereof, polyethylene and polypropylene. Examples of liquid-pervious layers are described in WO 99/57355 A1, EP 1 023 883 A2.

The liquid-impervious layer (B) generally consists of a film of polyethylene or polypropylene. A nonwoven may be laminated onto the layer (B) for better tactile properties on the outside.

Absorption and distribution layers (E) are typically produced from nonwovens which have very good wicking action, in order to absorb and to distribute the liquid rapidly. They also improve rewetting. When pressure on the diaper causes the water-absorbing composite to release liquid, the absorption and distribution layer (E) prevents this liquid from coming into contact with the skin of the user.

Suitable nonwovens are thermally bonded or resin-bonded fibers based on polypropylene and/or polyester fibers with a basis weight of 25 to 70 gms, for example CURADIS®, CURADIS® EPS, CURADIS® ATP and CURADIS® RB (Albis SPA, IT).

Further suitable absorption and distribution layers (E) are obtained by "airthroughbonding" and are obtainable under the ACQUITEX® (Texus SPA, IT) and DRY WEB® (Libeltex BVBA, NL) trademarks.

The water-absorbing composites produced by the process according to the invention have improved odor-inhibition compared to the composites produced by processes customary to date.

The water-absorbing polymer particles and composites are tested by means of the test methods described hereinafter.

Methods:

The measurements should, unless stated otherwise, be performed at an ambient temperature of 23±2° C. and a relative air humidity of 50±10%. The water-absorbing polymer particles are mixed thoroughly before the measurement.

Centrifuge Retention Capacity (CRC, Pad)

The centrifuge retention capacity (CRC) of the water-absorbing composites ("pads") is determined analogously to EDANA recommended test method No. WSP 241.2-05 "Centrifuge Retention Capacity" with the following changes:

- instead of the water-absorbing polymer particles (superabsorbent), one punched-out pad round, diameter 5 cm) is used per teabag, irrespective of the weight
- one (20×10) $cm^2$ teabag is used (point 6.1 of the method)
- only 5 teabags per liter of salt solution (point 8.6 of the method)
- the pad is pulled apart a little before the welding of the teabag
- a quintuple determination is carried out (point 9.3 of the method)

Centrifuge Retention Capacity (CRC,)

The centrifuge retention capacity (CRC) of the water-absorbing polymer particles is determined by EDANA recommended test method No. WSP 241.2-05 "Centrifuge Retention Capacity".

Absorbency Under a Load of 49.2 $g/cm^2$ (AUL 0.7 psi)

The absorbency under a load of 49.2 $g/cm^2$ (AUL 0.7 psi) of the water-absorbing polymer particles is determined analogously to EDANA recommended test method No. WSP 242.2-05 "Absorption under Pressure", except using a load of 49.2 $g/cm^2$ (AUL 0.7 psi) instead of a load of 21.0 $g/cm^2$ AUL 0.3 psi).

Saline Flow Conductivity (SFC)

The saline flow conductivity (SFC) of a swollen gel layer under pressure load of 63.3 $g/cm^2$ (0.9 psi) is, as described in EP 0 640 330 A1, determined as the gel layer permeability of a swollen gel layer of water-absorbing polymer particles, except that the apparatus described on page 19 and in FIG. 8 in the aforementioned patent application was modified in that the glass frit (40) is no longer used, the plunger (39) consists of the same polymer material as the cylinder (37) and now comprises 21 bores of equal size distributed uniformly over the entire contact surface. The procedure and the evaluation of the measurement remains unchanged from EP 0 640 330 A1. The flow rate is recorded automatically.

The saline flow conductivity (SFC) is calculated as follows:

$$SFC [cm^3 s/g] = (Fg(t=0) \times L0)/(d \times A \times WP),$$

where Fg(t=0) is the flow rate of NaCl solution in g/s, which is obtained by means of a linear regression analysis of the Fg(t) data of the flow determinations by extrapolation to t=0, L0 is the thickness of the gel layer in cm, d is the density of the NaCl solution in $g/cm^3$, A is the surface area of the gel layer in $cm^2$ and WP is the hydrostatic pressure over the gel layer in $dyn/cm^2$.

Bacteria-Induced Ammonia Release

DSM1 medium (Deutsche Sammlung von Mikroorganismen and Zellkulturen GmbH) was prepared from 5.0 g/l of peptone from meat (Merck KGaA; DE; Art. No. 1.07214) and 3.0 g/l of meat extract (Merck KGaA; DE; Art. No. 1103979) and adjusted to pH=7.0. 50 ml of DSM1 medium were inoculated to OD=0.1 with *Proteus mirabilis* ATCC 14153, and incubated in a 250 ml baffled Erlenmeyer flask at 37° C. and 220 rpm for 15 hours. The cultures thus produced had a cell density of about $10^9$ CFU/ml (OD=2.0-2.5).

The synthetic urine was prepared from 25 g/l of urea (sterile-filtered), 9.0 g/l of sodium chloride, 1 g/l of peptone from meat and 1 g/l of meat extract. The synthetic urine was autoclaved before addition of a sterile-filtered concentrated urea solution.

A 125 ml polypropylene histology beaker is autoclaved and a pad (diameter 5 cm) is placed into it. The amount of synthetic urine needed for absorption is added (calculated from the centrifuge retention capacity). The synthetic urine was inoculated beforehand with bacterial strain solution corresponding to a total concentration of approx. 106 CFU/ml. Immediately after addition, the lid provided with a diffusion test tube of the DRÄGer TUBE® Ammonia 20/a-D type (Art. No. 8101301, Drägerwerk AG & Co. KGaA; DE) is screwed on. The evolution of ammonia was observed at 37° C. over 48 hours.

EXAMPLE

Cellulose Fluff 1

Sheets of NB416 sulfate pulp (Weyerhaeuser Inc.; US) were broken down in a conventional KITCHENAID® Ultra Power blender at maximum power.

Cellulose Fluff 2

Cellulose fluff 1 was mixed cautiously but homogeneously with 0.5% by weight of zinc peroxide (56% pure by weight; Nitrochemie Aschau GmbH; DE) in a conventional KITCHENAID® Ultra Power blender, and then sprayed homogeneously with 0.1% by weight of a 50% by weight aqueous solution of PLURIOL® E 400 polyethylene glycol.

Water-Absorbing Polymer Particles 1

Conventional water-absorbing polymer particles of the HYSORB® B7065 type (BASF SE; DE) were used. HYSORB® B7065 is a crosslinked, partly neutralized polyacrylic acid with a degree of neutralization of 75 mol %. The polymer particles have been surface postcrosslinked with DENACOL® EX410 and have the following properties:

| | |
|---|---|
| CRC: | 30 g/g |
| AUL 0.7 psi: | 23 g/g |
| SFC: | $30 \times 10^{-7}$ |

Water-Absorbing Polymer Particles 2

200 g of water-absorbing polymer particles 1 were weighed into a glass bottle with 1.0 g of zinc peroxide (56% pure by weight; Nitrochemie Aschau GmbH; DE). Subsequently, this mixture was transferred into a large porcelain dish (internal diameter 16 cm) and triturated there for approx. 5 minutes. In addition, the samples were homogenized in a tumbling mixer at 46 rpm for another 20 minutes. Thereafter, 0.28 g of a 50% by weight aqueous solution of PLURIOL® E 400 (polyethylene glycol) was sprayed on while stirring.

Production of the Water-Absorbing Composites (General Production Method)

3.0 g of water-absorbing polymer particles are weighed onto weighing boats in six equal portions of 0.50+/−0.001 g.

4.5 g of cellulose fluff are divided into six equal portions of 0.75+/−0.01 g

The water-absorbing composite is produced as follows:

A tissue (SCA Hygiene Products AB; SE) is placed onto a rectangular wire mesh with a length of 17.5 cm and a width of 11 cm, the tissue projecting somewhat beyond the wire mesh. Above the wire mesh is a vertical shaft of the same dimensions. Within this shaft, approx. 75 cm above the wire mesh, rotates a brush installed lengthways. The brush has a length of 17.5 cm and a diameter of 10 cm. The brush rotates at 13.5 revolutions per second. Below the wire mesh with the tissue, vacuum is applied.

The first portion of cellulose fluff is applied to the rotating brush from above. After 25 seconds, the first portion of polymer in each case is metered from above onto the rotating brush. The metered additions of cellulose fluff and water-absorbing polymer particles are repeated twice more in total after 25 seconds each time. Subsequently, the wire mesh with the tissue is rotated horizontally by 180°.

Then the metered additions of cellulose fluff and water-absorbing polymer particles are repeated three times more in total, and the water-absorbing composite formed is pressed together by hand with a plunger having a length of 15 cm and a width of 8.5 cm, removed from the tissue and wrapped in a tissue (SCA Hygiene Products AB; SE) with a length of 37 cm and a width of 24 cm.

Composite 1

According to the general production method, cellulose fluff 2 and water-absorbing polymer particles 1 were used to produce a water-absorbing composite.

Composite 2

According to the general production method, cellulose fluff 1 and water-absorbing polymer particles 2 were used to produce a water-absorbing composite.

Composite 3

According to the general production method, cellulose fluff 1 and water-absorbing polymer particles 1 were used to produce a water-absorbing composite, and the rotation of the wire mesh by 180° was followed by homogeneous application of 15 mg of zinc peroxide (56% pure by weight; Nitrochemie Aschau GmbH; DE).

Production of the Diapers

One diaper in each case of the Pampers Simply Dry type, size 4, was opened cautiously, the absorbent core was completely removed and replaced in each case by one of the water-absorbing composites 1 to 3 produced. The w ater-absorbing composite was placed in the middle of each diaper.

A pad of diameter 5 cm was punched out of the middle of the diaper and then the pad was used to determine the bacteria-induced ammonia release.

TABLE 1

| Bacteria-induced ammonia release | |
|---|---|
| | Time until an ammonia release of 1500 ppm/h |
| Composite 1 | after 48 h still no ammonia detectable |
| Composite 2*) | 32.25 h |
| Composite 3*) | 30.75 h |

*)not inventive

The invention claimed is:

1. A process for producing odor-inhibiting water-absorbing composites comprising water-absorbing polymer particles and fibers, which comprises (a) premixing the fibers with at least one metal peroxide, metal hyperoxide, or metal ozonide, then (b) mixing the water-absorbing polymer particles with the premixture (a).

2. The process according to claim 1, wherein the metal peroxide is a peroxide of a metal of main group 1, of main group 2, and/or of transition group 2 of the Periodic Table of the Elements.

3. The process according to claim 1, wherein the metal peroxide comprises a peroxide of a metal of transition group 2 of the Periodic Table of the Elements.

4. The process according to claim 1, wherein the metal peroxide comprise zinc peroxide.

5. The process according to claim 1, wherein the composite comprises from 0.001 to 5% by weight of the metal peroxide, metal hyperoxide, or metal ozonide.

6. The process according to claim 1, wherein the fibers comprise cellulose fibers.

7. The process according to claim 1, wherein the composite comprises at most 70% by weight of fibers.

8. The process according to claim 1, wherein the water-absorbing polymer particles comprise to an extent of at least 50% by weight of polymerized acrylic acid and/or salts thereof.

9. The process according to claim 1, wherein the water-absorbing polymer particles have a centrifuge retention capacity of at least 15 g/g.

10. A composite prepared according to the process of claim 1.

11. A hygiene article comprising a composite produced according to claim 1.

12. The process according to claim 1 wherein the composite comprises from 0.01 to 3% by weight of the metal peroxide, metal hydroperoxide, or metal ozonide.

13. The process according to claim 1 wherein the composite comprises from 0.1 to 1.5% by weight of the metal peroxide, metal hydroperoxide, or metal ozonide.

14. The process according to claim 1 wherein the composite comprises from 0.2 to 0.8% by weight of the metal peroxide, metal hydroperoxide, or metal ozonide.

* * * * *